US008123773B1

(12) United States Patent
Shirley (10) Patent No.: US 8,123,773 B1
(45) Date of Patent: Feb. 28, 2012

(54) POSTPARTUM HEMORRHAGE BALLOON TAMPONADE CATHETER

(75) Inventor: Ben D. Shirley, Salt Lake City, UT (US)

(73) Assignee: Utah Medical Products Inc., Salt Lake City, UT (US)

( * ) Notice: Subject to any disclaimer, the term of this patent is extended or adjusted under 35 U.S.C. 154(b) by 553 days.

(21) Appl. No.: 12/207,578

(22) Filed: Sep. 10, 2008

(51) Int. Cl.
*A61M 29/00* (2006.01)

(52) U.S. Cl. .................... 606/193; 604/103.07

(58) Field of Classification Search .............. 606/191, 606/192, 193; 604/103.07
See application file for complete search history.

(56) References Cited

U.S. PATENT DOCUMENTS

| | | | |
|---|---|---|---|
| 3,152,592 A | | 10/1964 | Foley |
| 4,018,230 A | * | 4/1977 | Ochiai et al. .............. 606/193 |
| 4,137,922 A | * | 2/1979 | Leininger et al. .......... 606/193 |
| 5,419,763 A | * | 5/1995 | Hildebrand ................ 604/517 |
| 5,947,991 A | * | 9/1999 | Cowan ....................... 606/191 |
| 6,024,753 A | * | 2/2000 | Claren et al. .............. 606/193 |
| 6,520,977 B2 | | 2/2003 | Piraka |
| 6,648,842 B2 | * | 11/2003 | Horkel ........................ 601/45 |
| 6,676,680 B1 | | 1/2004 | Packer |
| 6,758,831 B2 | * | 7/2004 | Ryan ...................... 604/103.03 |
| 7,220,252 B2 | | 5/2007 | Shah |
| 2001/0007945 A1 | | 7/2001 | Piraka |
| 2003/0060800 A1 | * | 3/2003 | Ryan ........................... 604/515 |
| 2004/0030352 A1 | * | 2/2004 | McGloughlin et al. ....... 606/193 |
| 2004/0267378 A1 | * | 12/2004 | Gazi et al. ................. 623/23.67 |
| 2006/0235461 A1 | * | 10/2006 | Harter ........................ 606/193 |
| 2007/0239110 A1 | | 10/2007 | Shah |
| 2008/0027421 A1 | | 1/2008 | Vancelette |

OTHER PUBLICATIONS

Marcovici, Iacob et al., "Postpartum Hemorrhage and Intrauterine Balloon Tamponade, A Report of Three Cases," The Journal of Reproductive Medicine, vol. 2, No. 2, Feb. 1999, pp. 122 to 126.
Bowen, LW et al., "Use of a Large Foley Catheter Balloon to Control Postpartum Hemorrhage Resulting from a Low Placental Implantation, A Report of Two Cases," The Journal of Reproductive Medicine, Aug. 1985.
Goldrath, MH, "Uterine Tamponade for the Control of Acute Uterine Bleeding," American Journal Obstetrics Gynecology, Dec. 15, 1938, vol. 147(8), pp. 869 to 872.
DeLoor, Jeanette A. et al., "Foley Catheters for Uncontrollable Obstetric or Gynelogical Hemorrhage," The American College of Obstetricians Gynecologists, Jan. 1996.
Kauff, Noah D., "Intractable Bleeding Managed with Foley Catheter Tamponade after Dilation and Evacuation," American Journal Obstetrics Gynecology, Oct. 1994, pp. 957 to 958.
Marcovici, Iacob et al., "Postpartum Hemorrhage—A Review," Jurnalul de Chirurgie, Iasi, 2005, vol. 1, Nr. 4, Aug. 27, 2005, pp. 383 to 389.

(Continued)

*Primary Examiner* — Gary Jackson
*Assistant Examiner* — Katrina Stransky
(74) *Attorney, Agent, or Firm* — Kirton & McConkie; Evan R. Witt (57) ABSTRACT

A balloon tamponade catheter for controlling uterine postpartum hemorrhage has an elongated body with a balloon at a marginal distal end of the elongated body for insertion into the uterus. The balloon preferably has a pear-shaped appearance. The balloon may have a first hemisphere that is located on the catheter distal to second, smaller hemisphere. The first hemisphere has a plane of maximum diameter that is larger than the second hemisphere's plane of maximum diameter. Between the two planes of maximum diameter, the balloon comprises a transition section. In some cases, the transition section bows inward towards the elongated body when the balloon is uninflated and/or inflated. Additionally, the elongated body preferably does not extend distally past the distal end of the first hemisphere.

15 Claims, 3 Drawing Sheets

OTHER PUBLICATIONS

Mousa, HA et al., "Major Postpartum Hemorrhage," Current Opinions of Obstetrics and Gynecology, vol. 13(6), Dec. 2001, pp. 595 to 603.

Bakri, YN et al., "Tamponade-Balloon for Obstetrical Bleeding," International Journal of Gynecology and Obstetrics, vol. 74(2), Aug. 2001, pp. 139 to 142.

* cited by examiner

POSTPARTUM HEMORRHAGE BALLOON TAMPONADE CATHETER

BACKGROUND OF THE INVENTION

1. Field of the Invention

This disclosure relates to apparatus and methods for controlling postpartum hemorrhaging. More particularly, this disclosure discusses a pear-shaped balloon tamponade catheter for controlling uterine postpartum hemorrhaging.

2. Background and Related Art

Postpartum hemorrhage ("PPH") may be defined as excessive bleeding (a loss of more than 500 ml of blood) after childbirth. This excess and rapid blood loss can cause a severe drop in the mother's blood pressure and may lead to shock and even death if not treated properly. Indeed, PPH remains in the top five causes of maternal death worldwide. Moreover, using the aforementioned definition of PPH, it is estimated that PPH occurs in about 5%-10% of all births in both developed and underdeveloped countries. The basic causes of PPH are failure of the uterus to contract and retract (80-90%) as a result of obstructive blood clots, fibroids, tissue fragments, or other anomalies; uterine lacerations; uterine inversions; coagulation disorders; and other similar complications associated with childbirth.

Most of the deaths caused by PPH are considered preventable. In fact, PPH can be treated in a variety of manners. In one example, a uterine fundal massage can help to expel blood clots and encourage natural contraction and retraction of the uterine musculature. In another example, the administration of oxytocin can produce rapid, strong, and rhythmic contractions that aid hemostasis. However, in some cases, fundal massages and the administration of oxytocin are not effective at controlling PPH. In such cases, more invasive treatments may be required. For instance, the treatment of acute PPH may require a hysterectomy, major vessel embolization, and/or artery ligation (laparotomy). In some cases, a tamponade is used to control PPH or to buy time until a more invasive surgery can be performed. Historically, tamponade intervention has involved packing the uterus tight with several yards of gauze under general anesthesia. More recently, however, tamponade intervention has involved the use of a Foley catheter with a large bulb or multiple Foley catheters that are to be inflated within the uterus.

However, current tamponades are not without their shortcomings. By way of example, the bulbs of some tamponades are not shaped to provide an optimal pressure across surfaces of the uterus. Similarly, some tamponades comprise components that can come between the bulb and the uterus and thereby prevent the bulb from properly contacting the uterus. Accordingly, such bulbs may not control PPH as efficiently as possible. Thus, while apparatus and techniques currently exist that are used for the treatment of PPH, challenges still exist. Accordingly, it would be an improvement in the art to augment or even replace current apparatus or techniques with other apparatus and techniques.

BRIEF SUMMARY OF THE INVENTION

This disclosure discusses a balloon tamponade catheter for controlling uterine postpartum hemorrhaging. The balloon tamponade catheter includes a catheter body with an expandable balloon located distally on the catheter body for insertion into the uterus. Generally, the balloon has a substantially pear-shaped appearance when it is uninflated and/or inflated. While the balloon can achieve such an appearance in any suitable manner, in some cases, the balloon comprises a first hemisphere and a second smaller hemisphere. In such cases, the first hemisphere has a first plane of maximum diameter that is larger than the second hemisphere's second plane of maximum diameter. Moreover, in such cases, the first hemisphere is distally located on the catheter body with respect to the second hemisphere.

In some instances, the balloon comprises a transition section that spans between the first plane of maximum diameter and the second plane of maximum diameter. While the transition section can have any suitable shape, in some circumstances, as the transition section extends between a perimeter of the first plane and a perimeter of a second plane, at least a portion of the section bows in towards the catheter body. In one example, the transition section bows in towards the catheter when the interior pressure of the balloon is substantially equal to the pressure exerted on the exterior of the balloon. In another example, the transition section bows in towards the catheter when the balloon is inflated at or below a maximum volume.

The catheter body may comprise virtually any catheter body type that can be used to inflate, deflate, and/or insert the balloon into the uterus. In one example, the catheter comprises a dual-lumen catheter with a first lumen and a second lumen. In a non-limiting embodiment, the first lumen has an opening at the distal end of the catheter body. Accordingly, fluids or other materials may be passed through the first lumen to irrigate and/or to drain the uterus. The second lumen may comprise an aperture between the interior of the second lumen and the interior of the balloon. Thus, the second lumen is configured to allow the balloon to be inflated or deflated.

While the distal end of the catheter may extend to any desired location with respect to a distal end of the balloon's first hemisphere, the distal end may stop at or proximal to the distal end of the first hemisphere. In this manner, the distal end of the first hemisphere can contact the uterus without interference from the distal end of the catheter body.

The described balloon tamponade catheter may be able to contact and apply pressure to most if not all of the interior surfaces of the uterus. In this manner, the balloon tamponade catheter may effectively stop or control bleeding in patients with PPH. However, while the apparatus and methods of the present invention may be particularly useful in the area of controlling PPH, those skilled in the art can appreciate that the apparatus and methods can be used in a variety of different applications, including in controlling vaginal bleeding.

These features and advantages of the present invention will become more fully apparent from the following description and appended claims, or may be learned by the practice of the invention as set forth hereinafter.

BRIEF DESCRIPTION OF THE SEVERAL VIEWS OF THE DRAWINGS

In order that the manner in which the above-recited and other features and advantages of the invention are obtained and will be readily understood, a more particular description of the invention briefly described above will be rendered by reference to specific embodiments thereof that are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE INVENTION

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided, such as examples of suitable catheters, materials, apparatus, processes, methods, etc., to provide a thorough understanding of embodiments of the invention. One skilled in the relevant art will recognize, however, that the invention may be practiced without one or more of the specific details or methods, or with other methods, components, characteristics, materials, and so forth. In other instances, well-known structures, materials, or operations are not shown or described in detail to avoid obscuring aspects of the invention.

The embodiments of the present invention will be best understood by reference to the drawings, wherein like parts are designated by like numerals throughout. It will be readily understood that the components of the present invention, as generally described and illustrated in the Figures herein, could be arranged and designed in a wide variety of different configurations. Thus, the following more detailed description of the embodiments of the postpartum hemorrhage balloon tamponade catheter as represented in FIGS. 1 through 5, is not intended to limit the scope of the invention, as claimed, but is merely representative of the embodiments of the invention.

Figure 1:
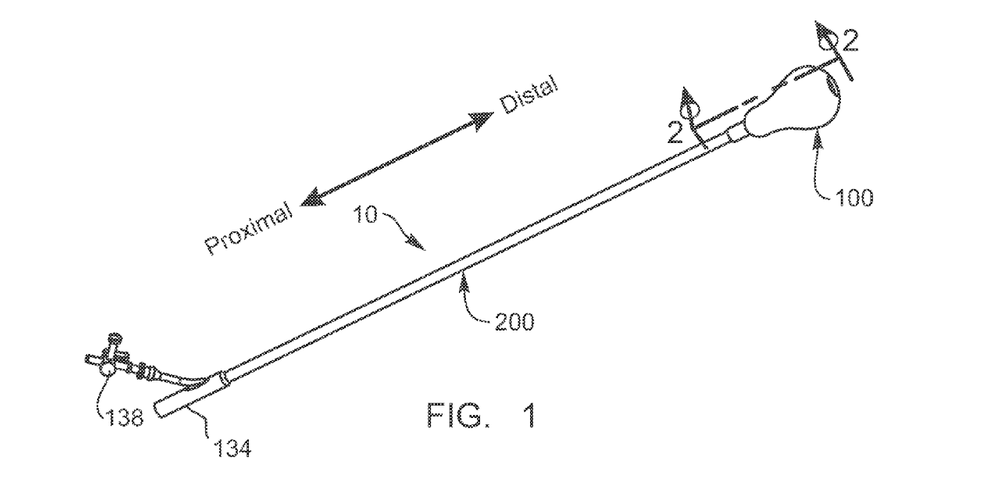
FIG. 1 illustrates some embodiments of a balloon tamponade catheter.

The present invention is drawn to a postpartum hemorrhage balloon tamponade catheter ("BT Catheter"). Generally, the BT Catheter is adapted so that a balloon located at a distal end of the catheter can be inserted into a uterus where the balloon can be inflated to apply pressure to an interior surface of the uterus. In this manner, the BT Catheter can reduce uterine bleeding and control PPH. While the BT Catheter may comprise any component that allows it to fulfill this or other similar functions, FIG. 1 shows a representative embodiment in which the BT Catheter 10 comprises an expandable balloon 100 and a catheter body 200. To provide a better understanding of the BT Catheter, the balloon and the catheter body are described below in more detail.

Figure 2:
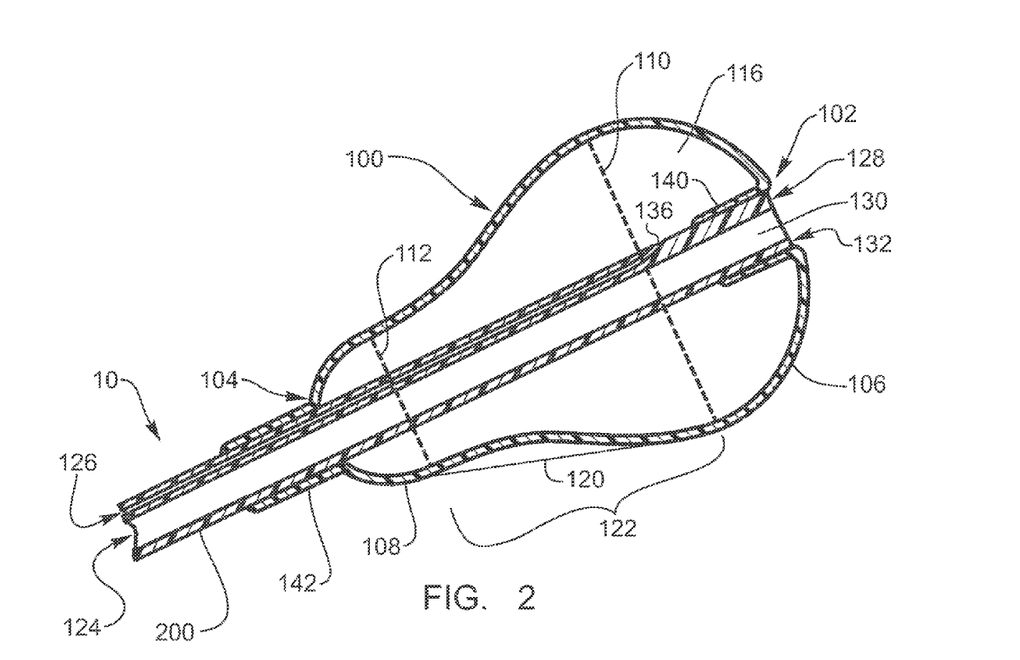
FIG. 2 illustrates a cross-sectional view through the balloon tamponade catheter of FIG. 1 along line 2-2.

The balloon may have any characteristic or component that allows it to be inserted into a uterus where it can be inflated to apply pressure to one or more internal uterine surfaces so as to reduce uterine bleeding or otherwise treat PPH. In one example, the balloon has a pear-shaped appearance. As used herein, the term pear-shaped may refer to a shape that bulges towards a distal end and tapers near a proximal end. By way of illustration, FIG. 2 shows a representative embodiment in which the pear-shaped balloon 100 is broad near its distal end 102 and tapered near its proximal end 104. Additionally, FIG. 2 shows that in some circumstances, the balloon 100 comprises two tiers. In particular, FIG. 2 shows some embodiments in which the balloon 100 comprises a first hemisphere 106 and a smaller second hemisphere 108. As shown in FIG. 2, the first hemisphere 106 comprises a substantially rounded portion that extends from the balloon's distal end 102 towards a first plane of maximum diameter 110. Similarly, FIG. 2 shows the second hemisphere 108 comprises a smaller, substantially rounded portion that extends from the balloon's proximal end 104 towards a second plane of maximum diameter 112.

The first and second hemisphere can have any characteristic that allows the balloon to have a substantially pear-shaped appearance. For instance, FIG. 2 shows the first plane of maximum diameter 110 is a portion of widest diameter for the rest of the first hemisphere 106. Similarly, FIG. 2 shows the second plane of maximum diameter 112 is a widest diameter of the second hemisphere 108. As shown in FIG. 2, in some instances, the second plane 112 is located at a position in the balloon 100 in which the second hemisphere begins to transition from its substantially semi-spherical shape and to flare out towards the first hemisphere.

Figure 3:
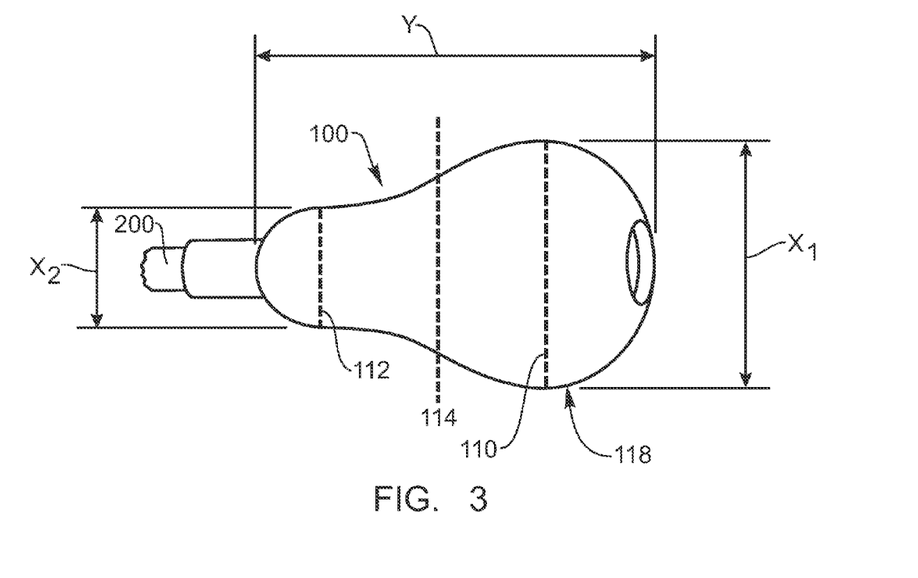
FIG. 3 illustrates a view of some embodiments of an uninflated pear-shaped balloon tamponade.

The first and second planes of maximum diameter can be located in any position that allows the balloon to have a substantially pear-shaped appearance. By way of example, FIG. 3 shows a non-limiting embodiment where the first plane of maximum diameter 110 is located distally with respect to a longitudinal midpoint 114 of the balloon 100. FIG. 3 further shows a non-limiting embodiment in which the second plane of maximum diameter 112 is located proximally on the catheter body with respect to the balloon's longitudinal midpoint 114.

Figure 4:
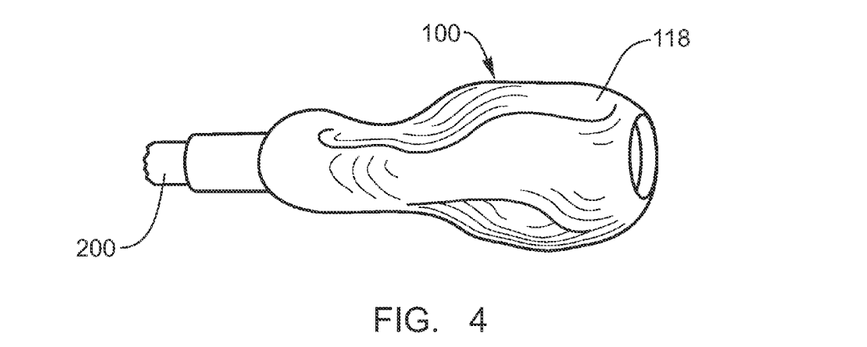
FIG. 4 illustrates a view of some embodiments a collapsed pear-shaped balloon tamponade.
Figure 5:
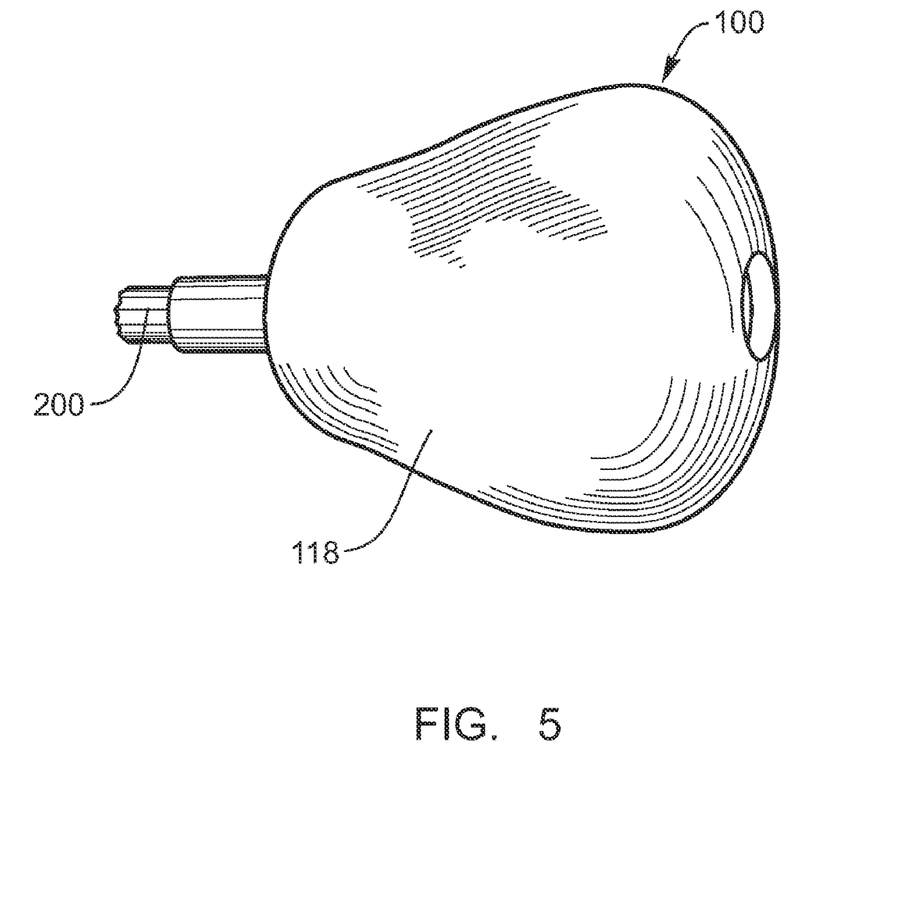
FIG. 5 illustrates view of some embodiments of an inflated pear-shaped balloon tamponade.

Because the balloon is expandable, to some extent, its shape depends on its internal pressure. Accordingly, the interior 116 of the balloon 100 (shown in FIG. 2) can have any suitable pressure that allows the balloon to be inserted into a uterus, apply pressure to one or more internal uterine surfaces, and/or to be withdrawn from the uterus. In one example, the balloon has an internal pressure that allows the balloon to be partially or completely "collapsed" by external pressures. For instance, FIG. 4 shows that, in some embodiments, when the balloon's internal pressure is lower than the atmospheric pressure that is exerted on the balloon's exterior surface 118, the balloon 100 is partially collapsed around the catheter body 200. In a second example, although the balloon is not inflated, per se, it has an internal pressure that is sufficient to prevent it from collapsing under atmospheric pressure. In other words, the balloon is "uninflated" when, as shown in FIG. 3, the balloon's internal pressure is substantially equal to the atmospheric pressure exerted on the balloon's exterior 118. In a third example, FIG. 5 shows some embodiments in which the balloon 100 is "inflated", or in which the balloon's interior pressure is greater than the atmospheric pressure exerted on the balloon's exterior surface 118.

When the balloon is uninflated, the interior of the balloon may have any volume that allows the balloon to have a substantially pear-shaped appearance. Indeed, in some embodiments, the uninflated balloon has an internal volume from about 40 to about 120 milliliters. In still other embodiments, the uninflated balloon has an internal volume that is from about 60 to about 100 milliliters. In yet other embodiments, the uninflated balloon comprises an internal volume that is from about 70 to about 90 milliliters. For instance, in some typical embodiments, the uninflated balloon has an internal volume of about 80 milliliters±5 milliliters.

When the balloon is inflated, it may have virtually any maximum internal volume that allows the balloon to apply pressure to internal uterine surfaces and reduce bleeding. In some embodiments, the balloon can be inflated to comprise a maximum volume from about 50 to about 1,000 milliliters. In other embodiments, the inflated balloon has a maximum internal volume of from about 100 to about 550 milliliters (e.g., about 500 milliliters). In still other embodiments, the balloon has a maximum internal volume from about 150 to about 350 milliliters. Indeed, in some preferred embodiments, the inflated balloon has a maximum internal volume of from about 200 to about 300 milliliters. For instance, in some typical embodiments, the balloon may be inflated to a maximum volume of about 250 milliliters±25 milliliters).

When the balloon is uninflated, the first and second planes of maximum diameter can have any diameter that allows the balloon to have a pear-shaped appearance. With respect to the first plane, in some embodiments, the uninflated balloon comprises a first plane of maximum diameter having a diameter X1 (illustrated in FIG. 3) that is from about 2 to about 7 centimeters. In other embodiments, the first plane of maximum diameter in the uninflated balloon has a diameter that is from about 4.1 to about 5.1 centimeters. In still other embodiments, the first plane has a diameter that is from about 4.3 to about 4.9 centimeters. Indeed, in some preferred embodiments, the first plane in the uninflated balloon has a diameter that is from about 4.5 to about 4.7 centimeters. For instance, the first plane in some typical embodiments of the uninflated balloon is about 4.6 centimeters±0.05 centimeters.

With respect to the second plane of maximum diameter in the uninflated balloon, in some embodiments, the second plane has a diameter X2 (illustrated in FIG. 3) that is from about 0.8 to about 3.8 centimeters. In other embodiments, the uninflated balloon comprises a second plane having a diameter that is from about 1.8 to about 2.8 centimeters. In still other embodiments, the second plane of the uninflated balloon has a diameter that is from about 2 to about 2.6 centimeters. Indeed, in some preferred embodiments, the second plane in the uninflated balloon has a diameter from about 2.2 to about 2.4 centimeters. For instance, the second plane of the uninflated balloon may have a diameter of about 2.3 centimeters±0.05 centimeters.

When the balloon is uninflated, the diameter of the first plane can be larger than the diameter of the second plane by any suitable ratio that gives the balloon a pear-shaped appearance and allows the balloon to act as intended. In some embodiments, the first plane in the uninflated balloon has a diameter that is from about 1.2 to about 2.8 times larger than the second plane's diameter. In other embodiments, the first plane's diameter in the uninflated balloon is from about 1.5 to about 2.5 times larger than the diameter of the second plane. In still other embodiments, the first plane in the uninflated balloon is from about 1.7 to about 2.3 times larger than the second plane's diameter. For instance, the diameter of the first plane in the uninflated balloon may be about 2 (±0.2) times larger than the diameter of the second plane.

When the balloon is inflated, the first and second planes of maximum diameter may have any diameter that allows the balloon to have a pear-shaped appearance. With respect to the diameter of the first plane in the inflated balloon, in some embodiments, the first plane comprises a diameter having a length selected from about 6.3 to about 11.5 centimeters; about 7.6 to about 10.2 centimeters; and about 8 to about 9 centimeters.

With respect to the diameter of the second plane in the inflated balloon, in some embodiments, the second plane has a diameter with a length selected from about 3.8 to about 10.9 centimeters; about 6.4 to about 9.6 centimeters; and about 7 to about 8 centimeters.

When the balloon is inflated, the diameter of the first plane can be larger than the diameter of the second plane by any suitable ratio that allows the balloon to have a pear-shaped appearance and perform its intended functions. Indeed, in some embodiments, in the inflated balloon, the diameter of the first plane is larger than the diameter of the second plane by a ratio that is selected from between about 1.1 and about 3, between about 1.1 and 1.6, and between about 1.1 and about 1.2.

In some embodiments, the balloon comprises a transition section 122 that extends between the first and second planes of maximum diameter. In such embodiments, the transition section can have any suitable shape that allows the balloon to have a pear-shaped appearance and to apply enough pressure to an internal uterine surface to treat PPH. FIG. 2 illustrates a taper line 120 that extends from a perimeter of the first plane 110 to a corresponding perimeter of the second plane 112. FIG. 2 further illustrates one example in which at least a portion of the transition section 122 bows inward from the taper line 120, towards the catheter body 200. In another example that is not illustrated, at least a portion of the transition section substantially follows the taper line so as to extend in a substantially straight line from a perimeter of the first plane to a perimeter of the second plane. In still another example that is not illustrated, at least a portion of the transition section can cross the taper line so as to bow away from the catheter body.

The balloon can have any suitable length that allows the BT Catheter to fulfill its intended purposes. In one example, the length Y (shown in FIG. 3) between the distal end 102 and the proximal end 104 of the uninflated balloon 100 is from about 5 to about 13 centimeters. In another example, the length between the distal and proximal end of the balloon is from about 6 to about 10 centimeters. In still another example, the length between the distal and proximal end of the balloon is from about 6.4 to about 9 centimeters. The length of the balloon may vary little, if any, when the balloon is inflated and/or collapsed.

The BT Catheter can comprise any catheter body that allows the balloon to be located at a distal end of the catheter body and to be inserted into a uterus. Some non-limiting examples of suitable catheters comprise a single-lumen and a dual-lumen catheter. For instance, FIGS. 1 and 2 show one presently preferred embodiment in which the catheter body 200 is a dual-lumen catheter comprising a first lumen 124 and a second lumen 126.

While the first lumen, or drain lumen, may comprise any component or characteristic suitable for use with the BT Catheter, in some embodiments, the first lumen comprises at least one opening that is disposed at or near the distal end 128 of the catheter body 200. By way of illustration, in FIG. 2 the first lumen 124 comprises an opening 130 at the catheter body's distal end 128. Additionally, in FIG. 2 shows the distal end 102 of the balloon 100 defines an aperture 132 that corresponds with the opening 130 of the first lumen 124. In embodiments where the first lumen and balloon respectively comprise an opening and an aperture, fluids or other materials may pass through the first lumen. For instance, fluids, such a sterile saline solution or another physiologic solution, can be passed through the first lumen to irrigate the uterus. In other instances, once the catheter is inserted into the uterus, fluids and/or other materials, such as blood, blood clots, irrigation fluid, and so forth, may be drained from the uterus through the first lumen. This drainage may allow the catheter to better contact internal uterine surfaces to reduce or prevent bleeding and bleeding diathesis.

In another example of a suitable component or characteristic of the first lumen, FIG. 1 shows some embodiments where the first lumen (not shown) of the catheter body 200 comprises a connecting mechanism 134. In such embodiments, the first lumen can comprise any connecting suitable for use with the BT Catheter, including a flared frictional fitting, a Luer lock fitting, and the like. Additionally, the connecting mechanism can connect the first lumen with any suitable apparatus, such as vessel to collect and/or measure fluids and materials that drain from the uterus, a vessel that can be used to irrigate the uterus, etc.

The second lumen, or inflation lumen, may comprise any component or characteristic that allows a distending medium (e.g., a sterile saline solution, water, etc.) to pass through the second lumen so as to inflate and/or deflate the balloon without unduly interfering with the operation of the BT Catheter. For instance, FIG. 2 shows some embodiments in which the second lumen 126 comprises at least one hole 136 that extends between the second lumen 126 and the interior 116 of the balloon 100.

In another example of a suitable component, the second lumen may comprise an inflation control valve. Such a valve can serve many purposes, including maintaining the balloon in an inflated state and controllably deflating the balloon when it is desired that the pressure supplied to the uterine cavity be reduced or altogether removed. The inflation control valve may comprise any suitable valve, including a ball valve, a needle valve, a flapper-style valve, a one-way valve, a two-way valve, an inline rotary valve, an auto-pressure sensing mechanism that prevents the balloon from being over inflated or will bleed off pressure as the uterus contracts, etc. By way of example, FIG. 1 shows some embodiments in which the control valve comprises an inline rotary valve 138.

In another example of a suitable component of the second lumen, the second lumen may comprise connecting portion that is adapted to connect the second lumen to an apparatus that can inflate and or deflate the balloon. For example, the second lumen may comprise flared friction fitting, a Luer lock fitting, and so forth. Also, some non-limiting examples of apparatus that can be attached to the connecting portion may include a syringe, a pump, an intravenous ("IV") bag, or another item that can be attached to the second lumen to inflate and/or deflate the balloon.

The distal end of the catheter body may be located in any suitable location with respect to the distal end of the first hemisphere. For example, the distal end of the catheter body may stop short of or be substantially even with the distal end of the first hemisphere. For instance, FIG. 2 shows some embodiments in which the distal end 128 of the catheter body is disposed substantially even with, and does not extend distally past, the balloon's distal end 102. In embodiments where the distal end of the catheter body does not extend distally past the distal end of the first hemisphere, the first hemisphere may be able to contact one or more internal uterine surfaces without the distal end of the catheter body coming between the distal end of the first hemisphere and the uterine surface (s). Accordingly, in such embodiments, the BT Catheter may further reduce bleeding and improve treatment of PPH.

In addition to the previously mentioned components, the BT Catheter can optionally comprise any other suitable component or characteristic that allows it to fulfill its intended purposes. In one example, the balloon is coated or impregnated with a hemostatic material, which may help control bleeding when the balloon contacts internal uterine surfaces. In another example, the BT Catheter comprises a rigid delivery sheath through which at least a portion of the catheter extends. In another example, however, the catheter body comprises a substantially rigid portion that may allow the catheter body to maintain its shape so the balloon can be easily guided into the uterus. In still another example, the balloon may have any suitable thickness or Shore durometer measurement. For instance, the balloon may have a thickness selected from about 0.38 millimeters to about 0.89 millimeters and about 0.43 to about 0.69 millimeters. Similarly, the balloon material may have a Shore durometer measurement selected from about 15 to about 4 and about 20 to about 35 on the A scale.

The components of the BT Catheter may be fabricated of a variety of materials suitable for medical and health care applications. For example, the balloon may be fabricated from an expandable material, including, but not limited to, polyurethane, silicone, or another medical-grade elastomeric material. In another example, the catheter body may comprise medical-grade nylon, polyurethane, polyethylene, polyvinyl chloride, silicon, natural rubber, synthetic rubber, or other suitable material.

The BT Catheter can be made using any known or novel fabrication technique. For example, the balloon can be molded or extruded as known in the art. Moreover, the balloon can be attached to the catheter body in any suitable manner. For example, the balloon can be attached to the catheter body by adhesive bonding, heat sealing, chemical sealing, mechanical sealing, combinations thereof, or any other suitable sealing mechanism. For instance, FIG. 2 shows some embodiments in which the distal end 102 of the balloon 100 is attached to the catheter body 200 with an adhesively bonded internal seal 140. Similarly, FIG. 2 shows some embodiments where the proximal end 104 of the balloon 100 is attached to the catheter body 200 with an adhesively bonded external seal 142.

The BT Catheter can be used in any suitable manner that allows it to apply pressure to one or more internal uterine surfaces and, thereby, to treat PPH. Indeed, methods for using tamponade catheters are well known in the art. Nevertheless, in order to better explain the BT Catheter, a non-limiting example of the BT Catheter's use is given herein.

In this example, the BT Catheter is inserted transvaginally through the cervix and into the uterus. After the entire balloon has been inserted past the cervical canal and internal OS, the pear-shaped balloon is progressively inflated to apply pressure to one or more internal uterine surfaces. In some cases, the balloon is inflated so as to substantially fill the uterus. For instance, the approximate uterine volume can be determined by ultrasound or direct examination, and the balloon can be inflated so as to have a similar volume. In other cases, however, the balloon is simply inflated until fluid drainage from the uterus stops.

Once inflated, a fluid collection bag may be attached to the first lumen so that hemostasis can be monitored. However, if there is no drainage through the first lumen and/or the fundus increases in height, the first lumen may be flushed with a solution (e.g., a sterile saline solution).

The inflated balloon can be left in the patient and monitored for any suitable period of time (e.g., less than 24 hours). Once the BT Catheter is to be removed from the uterus, the pear-shaped balloon is slowly deflated. Once deflated to the collapsed or uninflated state, the balloon and catheter body can be retracted from the uterus and vaginal canal.

As described, the BT Catheter can have several noteworthy characteristics. For instance, the pear shape of the balloon may allow the balloon to contact a larger portion of the interior uterine surfaces than some conventional apparatus used that are used to control PPH. Similarly, the balloon's pear shape may allow the balloon to apply a more even pressure across the internal surfaces of the uterus. For instance, the balloon's pear shape may allow the balloon to apply substantially the same pressure (e.g., $N/m^2$, $dynes/cm^2$, p.s.i., etc.) to the uterus near the cervix as it does at the opposite end of the uterus. Accordingly, the BT catheter may control bleeding and PPH better than some conventional apparatus. Additionally, because the balloon may be inserted into the uterus without surgery, the use of BT Catheter may be less invasive than some methods and may not require the use of anesthetics.

While specific embodiments of the present invention have been illustrated and described, numerous modifications come to mind without significantly departing from the spirit of the invention, and the scope of protection is only limited by the scope of the accompanying claims.

The invention claimed is:

1. A balloon tamponade catheter for controlling postpartum hemorrhaging, the balloon tamponade catheter comprising:
   a catheter having a proximal end, a distal end, and at least two lumens, wherein one lumen is a drain lumen which opens from the distal end of the catheter to allow fluid communication between the drain lumen and a uterus; and
   an expandable pear-shaped balloon attached at the marginal distal end of the catheter, the balloon having a first hemisphere disposed on the catheter distal to a second hemisphere, wherein the first hemisphere has a first plane of maximum diameter having a diameter that is greater than a second plane of maximum diameter of the second hemisphere, and
   wherein the catheter comprises an inflation lumen that opens into an interior of the balloon to enable passage of a distending medium to inflate and deflate the balloon, wherein the balloon is configured to be inflated with the distending medium to a maximum volume between about 100 milliliters and about 550 milliliters.

2. The balloon tamponade catheter of claim 1, wherein the balloon further comprises a transition section that extends between the first hemisphere and the second hemisphere, and wherein at least a portion of the transition section bows inward towards the catheter between the first plane maximum diameter and the second plane of maximum diameter.

3. The balloon tamponade catheter of claim 1, wherein the distal end of the catheter does not extend distally past a distal end of the first hemisphere.

4. The balloon tamponade catheter of claim 1, wherein the pear shape allows the balloon to apply a substantially even pressure across most, if not all, of the uterus' internal surfaces.

5. The balloon tamponade catheter of claim 1, wherein the balloon is configured to be inflated with the distending medium to a maximum volume selected from:
   a. between about 150 milliliters and about 350 milliliters; and
   b. between about 200 milliliters and about 300 milliliters.

6. The balloon tamponade catheter of claim 1, wherein when the balloon is uninflated, the first plane of maximum diameter is larger than the second plane of maximum diameter by a ratio selected from:
   a. between about 1.2 and about 2.8;
   b. between about 1.5 and about 2.5; and
   c. between about 1.7 and about 2.3.

7. The balloon tamponade catheter of claim 1, wherein when the balloon is uninflated, the balloon comprises an interior volume selected from:
   a. between about 40 and about 120 milliliters;
   b. between about 60 and about 100 milliliters; and
   c. between about 70 and about 90 milliliters.

8. The balloon tamponade catheter of claim 1, wherein when the balloon is uninflated, the first plane of maximum diameter has a diameter selected from:
   a. between about 4.1 centimeters and about 5.1 centimeters;
   b. between about 4.3 centimeters and about 4.9 centimeters; and
   c. between about 4.5 centimeters and about 4.7 centimeters.

9. The balloon tamponade catheter of claim 8, wherein when the balloon is uninflated, the second plane of maximum diameter has a diameter selected from:
   a. between about 1.8 centimeters and about 2.8 centimeters;
   b. between about 2 centimeters and about 2.6 centimeters; and
   c. between about 2.2 centimeters and about 2.4 centimeters.

10. A balloon tamponade catheter for controlling postpartum hemorrhaging, the balloon tamponade catheter comprising:
    a catheter body having a proximal end, a distal end, and at least two lumens; and
    an expandable pear-shaped balloon attached at the distal end of the catheter body, the balloon having a first hemisphere disposed on the catheter body distal to a second hemisphere with a transition portion between the first and second hemisphere,
    wherein when the balloon is uninflated, the first hemisphere has a first plane of maximum diameter that is greater than a second plane of maximum diameter of the second hemisphere by a ratio of between about 1.2 and about 2.8,
    wherein the transition portion bows inward towards the catheter body between the first plane of maximum diameter and the second plane of maximum diameter,
    wherein the distal end of the catheter body does not extend distally past a distal end of the first hemisphere,
    wherein the balloon tamponade catheter comprises an inflation lumen that opens into an interior of the balloon to enable passage of a distending medium to inflate and deflate the balloon, wherein the balloon is configured to be inflated with the distending medium to a maximum volume between about 100 milliliters and about 550 milliliters, and
    wherein a drain lumen opens from the distal end of the catheter body to allow fluid communication between the drain lumen and a uterus.

11. The balloon tamponade catheter of claim 10, wherein the balloon is configured to be inflated with the distending medium to a maximum volume selected from:
    a. between about 150 milliliters and about 350 milliliters; and
    b. between about 200 milliliters and about 300 milliliters.

12. The balloon tamponade catheter of claim 10, wherein when the balloon is uninflated, the first plane of maximum diameter is larger than the second plane of maximum diameter by a ratio selected from:
    a. between about 1.5 and about 2.5;
    b. between about 1.7 and about 2.3; and
    c. between about 1.8 and about 2.2.

13. The balloon tamponade catheter of claim 10, wherein when the balloon is uninflated, the balloon comprises an interior volume selected from:
    a. between about 40 and about 120 milliliters;
    b. between about 60 and about 100 milliliters; and
    c. between about 70 and about 90 milliliters.

14. The balloon tamponade catheter of claim 10, wherein when the balloon is uninflated, the first plane of maximum diameter has a diameter selected from:

a. between about 4.1 centimeters and about 5.1 centimeters;
b. between about 4.3 centimeters and about 4.9 centimeters; and
c. between about 4.5 centimeters and about 4.7 centimeters.

15. The balloon tamponade catheter of claim 10, wherein when the balloon is uninflated, the second plane of maximum diameter has a diameter selected from:

a. between about 1.8 centimeters and about 2.8 centimeters;
b. between about 2 centimeters and about 2.6 centimeters; and
c. between about 2.2 centimeters and about 2.4 centimeters.

* * * * *